United States Patent
Rajaiah et al.

(10) Patent No.: US 6,500,406 B1
(45) Date of Patent: Dec. 31, 2002

(54) DENTURE CARE COMPOSITIONS AND KITS

(75) Inventors: Jayanth Rajaiah, Loveland, OH (US); Lisa Catron Ernst, Cincinnati, OH (US); Ann Maria Case, Cincinnati, OH (US); Thinh Nguyen Ha, Cincinnati, OH (US); William Michael Glandorf, Mason, OH (US); Christopher Robert Mayer, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/085,383

(22) Filed: Feb. 28, 2002

Related U.S. Application Data

(60) Provisional application No. 60/276,976, filed on Mar. 19, 2001, and provisional application No. 60/276,978, filed on Mar. 19, 2001.

(51) Int. Cl.[7] .............................. C11D 1/02; A61K 7/16
(52) U.S. Cl. ..................... 424/49; 510/117; 523/120; 134/2; 134/42
(58) Field of Search ................ 424/49–58; 510/116, 510/117; 134/2, 42

(56) References Cited

U.S. PATENT DOCUMENTS

| | | | | |
|---|---|---|---|---|
| 3,652,420 A | * | 3/1972 | Hill | 510/116 |
| 4,061,780 A | * | 12/1977 | Yoshida et al. | 424/358 |
| 4,108,823 A | * | 8/1978 | Yoshimura et al. | 523/120 |
| 4,158,543 A | * | 6/1979 | Orlowski | 8/137 |
| 4,495,314 A | | 1/1985 | Keegan | |
| 4,511,486 A | * | 4/1985 | Shah | 134/42 |
| 4,554,154 A | | 11/1985 | White | |
| 4,613,646 A | * | 9/1986 | Sandvick | 524/476 |
| 4,701,223 A | * | 10/1987 | Eoga | 134/2 |
| 4,807,649 A | * | 2/1989 | Eoga | 134/2 |
| 4,810,407 A | * | 3/1989 | Sandvick | 252/90 |
| 4,880,702 A | * | 11/1989 | Homan et al. | 428/354 |
| 4,948,580 A | * | 8/1990 | Browning | 514/772.5 |
| 5,051,130 A | * | 9/1991 | Futami et al. | 106/35 |
| 5,114,718 A | | 5/1992 | Damani | |
| 5,185,386 A | | 2/1993 | Cohen et al. | |
| 5,204,390 A | * | 4/1993 | Szymanski et al. | 524/91 |
| 5,449,473 A | * | 9/1995 | Bunczk et al. | 252/104 |
| 5,496,541 A | | 3/1996 | Cutler | |
| 5,543,443 A | | 8/1996 | Rajaiah et al. | |
| 5,648,326 A | * | 7/1997 | Sramek | 510/284 |
| 5,652,208 A | * | 7/1997 | Sramek | 510/284 |
| 5,656,286 A | * | 8/1997 | Miranda et al. | 424/449 |
| 5,888,602 A | * | 3/1999 | Davis et al. | 428/40.1 |
| 5,900,230 A | | 5/1999 | Cutler | |
| 5,965,255 A | * | 10/1999 | Ichimura et al. | 428/353 |
| 6,069,188 A | | 5/2000 | Rajaiah et al. | |
| 6,103,266 A | * | 8/2000 | Tapulsky et al. | 424/484 |
| 6,112,477 A | * | 9/2000 | Spinks | 52/172 |
| 6,194,364 B1 | * | 2/2001 | Glenn | 510/130 |

FOREIGN PATENT DOCUMENTS

| | | | |
|---|---|---|---|
| CA | 2031121 | | 6/1991 |
| DE | 25 58 602 C3 | | 6/1977 |
| DE | 25 58 602 A1 | | 6/1977 |
| JP | 53076591 A | * | 7/1978 |
| JP | 57-058529 | | 4/1982 |
| JP | 4-149110 | | 5/1992 |
| JP | 9-012419 | | 1/1997 |
| JP | 409012419 A | * | 1/1997 |
| JP | 12-126206 | | 5/2000 |
| JP | 200126206 A | * | 5/2000 |
| JP | 2001002543 A | * | 1/2001 |

* cited by examiner

*Primary Examiner*—Shep K. Rose
(74) *Attorney, Agent, or Firm*—Andrea L. Winslow

(57) ABSTRACT

A non-self-supporting denture care composition comprises polybutene with a molecular weight of about 300 to about 3000 and a denture care active. The denture care composition may further comprise a denture care carrier. Kits comprising polybutene, a container and instructions for use or an applicator for applying the composition directly to the denture surface are also disclosed. The polybutene composition of the kits can further comprise a denture care active.

15 Claims, No Drawings

DENTURE CARE COMPOSITIONS AND KITS

CROSS-REFERENCE TO RELATED APPLICATIONS

This application claims the benefit of U.S. Provisional Application, 60/276,976, filed Mar. 19, 2001 and U.S. Provisional Application 60/276,978, also filed Mar. 19, 2001.

FIELD OF THE INVENTION

The present invention relates to a denture care composition and denture care kit providing prolonged release of therapeutic, prophylactic and cosmetic actives to the oral cavity and inhibiting the buildup of plaque and other debris and on the dentures and other hard surfaces temporarily fixed within the oral cavity.

BACKGROUND OF THE INVENTION

Denture care products by which various denture care actives can be delivered to the hard surface of the artificial teeth have been previously known. For example, effervescent denture cleansing tablets, which require the artificial teeth to soak for a period of time, work to remove plaque and debris that has built up on the denture or plate. It is well known that denture care products can provide both therapeutic and cosmetic benefits to consumers. However, such conventional denture care products typically do not maintain actives in the oral cavity long enough to optimally enhance or prolong the therapeutic, prophylactic and/or cosmetic benefits provided by the actives. In order to provide a composition with sufficient substantivity to provide sustained release of a denture care active, the use of polybutene in a denture care composition is herein disclosed.

Polybutene is recognized as a component of denture adhesives and as a gum base. U.S. Pat. No. 5,880,172, issued Mar. 3, 1999, to Rajaiah, et al., discloses a self-supporting denture adhesive that is peelable for easy removal, which incorporates polybutene as an optional ingredient. U.S. Pat. No. 5,496,541, issued Mar. 5, 1996, to Cutler, relates to a dentifrice chewing gum and teaches the use of polybutene as an optional gum base. Such known applications often employ higher molecular weight polybutene in order to achieve the desired result.

In the present invention lower molecular weight polybutene is incorporated in the denture care composition and kit to provide a protective coating on the artificial teeth. The lower molecular weight polybutene is a flowable liquid that achieves good coating of the denture and is extremely substantive. Where a denture care active is incorporated in the present invention sustained release of the denture care active is achieved.

The present invention provides denture care kits and a denture care composition that effectively coat the dentures, dental plates, and other hard surfaces temporarily fixed within the oral cavity and thereby prevents the buildup of plaque and other debris. This coating works to inhibit and prevent staining of the denture and to treat the oral cavity. This coating also provides a slick, smooth feel to the artificial hard surfaces of the oral cavity which consumers view as an indicator of clean teeth. A therapeutic, cosmetic or prophylactic denture care active can be included in the composition of the present invention.

SUMMARY OF THE INVENTION

This invention relates to a non-self-supporting denture care composition comprising polybutene with a molecular weight of about 300 to about 3000 and one or more denture care actives. The denture care actives are selected from the group consisting of anti-calculus agents; fluoride ion sources; stannous ion sources; whitening agents; anti-microbial and anti-plaque agents; anti-inflammatory agents; nutrients; antioxidants; antiviral agents; anti-fungal agents; analgesic and anesthetic agents; H-2 antagonists; fragrances and sensates; components other than polybutene which impart a clean feel to the teeth; pigments, dyes, lakes and colorants; and mixtures thereof. When desired, a viscosity modifier, flavorant, or sweetener may optionally be incorporated in the present invention. The composition is essentially free of a mucoadhesive. The denture care composition may further comprise a denture care carrier.

This invention also relates to a denture care kit comprising polybutene with a molecular weight of about 300 to about 3000, a container and instructions for use. A denture care kit comprising polybutene with a molecular weight of about 300 to about 3000 and an applicator for applying the composition directly to the denture surface is also disclosed. In one embodiment the polybutene component of the kits further comprise a denture care active.

DETAILED DESCRIPTION OF THE INVENTION

Definitions

The term "dentures", as used herein, is meant to include dentures, dental plates, bridges, artificial teeth and other hard surfaces of dental appliances which are temporarily fixed within the oral cavity and which are typically removed from the oral cavity for cleaning.

The term "denture care carrier" as used herein means any safe and effective non-aqueous materials for use in the compositions of the present invention.

The term "container" as described herein, means a jar, cup, can, tube, aerosol can, tub, pump, bottle or any other liquid holding or dispensing means.

"Tartar" and "calculus" are used interchangeably and refer to mineralized dental plaque biofilms.

By "safe and effective amount", as used herein, is meant an amount of an agent (e.g., anti-calculus agent) high enough to significantly improve the condition to be treated, but low enough to avoid serious side effects (at a reasonable benefit/risk ratio), within the scope of sound medical/dental judgment. The safe and effective amount of an agent (e.g., anti-calculus agent) may vary with the particular condition being treated, the age and physical condition of the patient being treated, the severity of the condition, the duration of treatment, the nature of concurrent therapy, the specific form of the source employed, and the particular vehicle from which the agent is applied.

The term "non-self supporting" is used to describe a composition that lacks integrity and strength. In the instant case, this means that the composition is unable to be detached as one solid piece from the teeth even after several hours of use in the mouth. The composition cannot be cut and formed into definite shapes, such as a sheet or cone, which maintain their initial dimensions.

The term "mucoadhesive" or "bioadhesive" as used herein refers to the phenomenon where a natural or synthetic substance applied to a wet mucosal epithelium adheres, usually creating a new interface, to the mucous layer. (*CRC Critical Review in Ther. Drug Carrier*, Vol.5, Issue 1, p.21 (1988)). Generally, mucoadhesion can be achieved via physical or chemical processes, or both. This mechanism is described in *Journal of Controlled Release*, Vol.2, p257 (1982) and *Journal of Controlled Release*, Vol.18 (1992) p. 249. The above references are incorporated by reference herein in their entirety.

The term "unit dose form" refers to physically discrete units suitable as unitary dosages for human subjects and other mammals, each containing a predetermined quantity of active material calculated to produce the desired therapeutic effect.

The term "viscosity" as used herein refers to kinematic viscosity, measured using the standard test method for Kinematic Viscosity of Transparent and Opaque Liquids (the Calculation of Dynamic Viscosity), ASTM D-445. As reported, viscosity is measured at 99° C. (210° F.) unless otherwise indicated. A sample is placed in a U-shaped "Cannon-Fenske" type viscometer (for transparent liquids) tube and submerged into a constant temperature bath. Flow is timed between two marks on the tube and viscosity is determined by simple calculations dependent on time and a standard factor supplied by the tube manufacturer.

"Molecular weight", as referred to herein, is reported as a number average, determined using gel permeation chromatography. The number average molecular weight, or arithmetic mean, is a function of the number of molecules in a given mass of polymer. It is represented by the formula:

$$M_n = \frac{\Sigma N_i M_i}{\Sigma N_i} = \Sigma n_i M_i$$

where $N_i$, represents the number of molecules present for a given molecular weight, $M_i$ and $n_i = N_i | \Sigma N_i$ is the number fraction of molecular weight, $M_i$.

Percentages and ratios herein are by weight of total composition, unless otherwise indicated.

Polybutene

Polybutene is a viscous copolymer of isobutylene and butene monomers. "Polybutene", as used herein, refers to both hydrogenated (CAS #68937-10-0) and unhydrogenated (CAS #9003-29-6) forms of the polymer. Polybutene is a viscous, colorless, non-drying, liquid polymer. Polybutenes range from a flowable liquid to a near semi-solid state. Polybutenes are clear, odorless, chemically stable, resistant to oxidation by light and heat, non-toxic and non-hazardous.

In the present invention, a composition comprising polybutene with a molecular weight of about 300 to about 3000 and a denture care active is disclosed. In one embodiment, the composition comprises, a denture care active, a denture care carrier and polybutene with a molecular weight of about 300 to about 3000. The present invention also relates to a denture care kit comprising polybutene with a molecular weight of about 300 to about 3000, a container, and instructions for use. A denture care kit comprising polybutene with a molecular weight of about 300 to about 3000 and an applicator for applying the composition directly to the denture surface is also disclosed.

The compositions and kits of the present invention comprise polybutene, generally of a lower molecular weight from about 300 to about 3000, in another embodiment from about 500 to about 2200, and in another embodiment from about 750 to about 1500. The viscosity of the polybutene disclosed herein, ranges from about 30 cSt (centi Stoke) measured at 38° C. to about 4,500 cSt measured at 99° C., in another embodiment from about 200 cSt measured at 38° C. to about 3,500 cSt measured at 99° C., and in another embodiment from about 75 cSt measured at 99° C. to about 700 cSt measured at 99° C. Polybutene comprises from about 0.01% to about 100%, by weight of the composition, in another embodiment from about 1% to about 100%, in yet another embodiment from about 50% to about 100%.

The lower molecular weight polybutene of the present invention does not exhibit elastomeric properties. Elastomers are amorphous polymers that have the ability to stretch out and spring back to their original shapes. Such elastomeric polymers must have a modest amount of cross-linking to prevent the polymeric chains from slipping over one another, and the chains must have an irregular shape to prevent the formation of crystalline regions within the polymeric chains. Synthetic elastomers, are described in more detail in Kirk-Othmer, Encyclopedia of Chemical Technology, Fourth Edition, Volume 8, Wiley-Interscience Publishers (1996), pages 934–955, incorporated herein by reference in its entirety, including all references incorporated into Kirk-Othmer. The polybutene utilized in the present invention is not cross-linked and does not exhibit rubbery or elastic behavior. When subjected to a stretching or bending force, the polybutene herein does not return to its original shape upon the removal of the force.

Lower molecular weight polybutene (Molecular Weight= 300–3000), which is a flowable liquid known for its adhesive properties, is actually non-mucoadhesive. That is, the polybutene, while displaying excellent adhesion properties on the hard surfaces of the oral cavity, will not significantly adhere to the mucosa or wet, soft tissue of the mouth. In fact, polybutene is extremely substantive when applied to the denture, making it suitable for once daily application and treatment. High retention of the polybutene is achieved, even when thorough brushing has occurred. Thus, the polybutene, once applied to the denture surface, is long lasting, and rinse resistant, which allows for sustained release of certain optional denture care actives. Importantly, the compositions of the present invention are not self-supporting neither before, during, or after application to the denture.

Once applied to the artificial teeth, the polybutene has a very smooth, slick texture, perceived by the consumer as a desirable, clean feeling. The polybutene acts as a lubricant and reduces the friction normally produced when the tongue slides over these surfaces.

Suitable polybutenes for use herein include, but are not limited to: Indopol L-14, Molecular Weight ("MW")=370; Indopol L-50, MW=455; Indopol L-65, MW=435; Indopol L-100, MW=510, H-15, MW=600; H-25, MW=670; H-35, MW=725; H-40, MW=750; H-50, MW=815; H-100, MW=940; H-300, MW=1330; H-1500, MW=2145; H-1900, MW=2270; Panalane L-14E, MW=370; Panalane H-300E, MW=1330; all trade names of BP Amoco Chemicals (Chicago, Ill.). Other suitable grades of polybutene include Parapol 450, MW=420; Parapol 700, MW=700; Parapol 950, MW=950; Parapol 1300, MW=1300; and Parapol 2500, MW=2700; all trade names of ExxonMobil Corporation.

Denture Care Actives

The denture care compositions of the present invention may contain a denture care active in unit dose form where, upon directed use, the benefit sought by the wearer is promoted without detriment to the oral cavity. Examples of the dental conditions these actives address include, but are not limited to, appearance and structural changes to teeth, treatment and prevention of plaque, calculus, cavities in remaining natural teeth, inflamed and/or bleeding gums, gingivitis, fungal infections such as candida, mucosal wounds, lesions, ulcers, aphthous ulcers, cold sores, tooth abscesses, and the elimination of mouth malodor resulting from the conditions above and other causes such as microbial proliferation.

Suitable denture care active ingredients include any material that is generally considered safe for use in the oral cavity and that provides changes to the overall appearance and/or health of the oral cavity. The level of denture care active in the present invention is generally, unless otherwise noted, from about 0.001% to about 90%, in one embodiment from about 0.01% to about 50%, in another embodiment from about 0.1% to about 30%, by weight of the composition. Where the denture care actives are in particulate form, a suitable particle size for use in the present invention is from about 0.01 microns to about 1000 microns, in one embodiment from about 0.1 microns to 500 microns, in another embodiment from about 1 to about 100 microns. The denture care composition of the present invention may include many of the denture care actives previously disclosed in the art. The following is a non-limiting list of denture care actives that may be used in the present invention.

The present compositions may comprise at least one anti-calculus (i.e. anti-tartar) agent, present at a level from about 0.001% to about 50%, by weight of the composition, in another embodiment from about 0.01% to about 25%, and in yet another embodiment from about 0.1 to about 15%. The anti-calculus agent should be essentially compatible with the other components of the invention. The anti-calculus agent may be selected from the group consisting of polyphosphates (including pyrophosphates) and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof. In one embodiment, the salts are alkali metal salts. Polyphosphates are generally employed as their wholly or partially neutralized water-soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. Polyphosphates larger than tetrapolyphosphate usually occur as amorphous glassy materials. In one embodiment the polyphosphates are those manufactured by FMC Corporation, which are commercially known as Sodaphos (n≈6), Hexaphos (n≈13), and Glass H (n≈21, sodium hexametaphosphate), and mixtures thereof. The pyrophosphate salts useful in the present invention include, alkali metal pyrophosphates, di-, tri-, and mono-potassium or sodium pyrophosphates, dialkali metal pyrophosphate salts, tetraalkali metal pyrophosphate salts, and mixtures thereof. In one embodiment the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof. Polyolefin sulfonates include those wherein the olefin group contains 2 or more carbon atoms, and salts thereof. Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof, azacyclohexane-2,2-diphosphonic acid, azacyclopentane-2,2-diphosphonic acid, N-methyl-azacyclopentane-2,3-diphosphonic acid, EHDP (ethane-1-hydroxy- 1,1-diphosphonic acid), AHP (azacycloheptane-2, 2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts. Polyolefin phosphates include those wherein the olefin group contains 2 or more carbon atoms. Polypeptides include polyaspartic and polyglutamic acids.

Fluoride ion sources are known for use in denture care compositions as anti-caries agents for remaining natural teeth and may optionally be incorporated within the present invention. Application of fluoride ions to the dental enamel of natural teeth serves to protect those teeth against decay. A wide variety of fluoride ion-yielding materials can be employed as sources of soluble fluoride in the instant compositions. Examples of suitable fluoride ion-yielding materials are found in Briner, et al., U.S. Pat. No. 3,535,421 and Widder, et al., U.S. Pat. No. 3,678,154. Preferred fluoride ion sources for use herein include sodium fluoride, potassium fluoride, stannous fluoride, mono fluoro phosphate (MFP), and ammonium fluoride. In one embodiment sodium fluoride is the fluoride ion source. The instant invention provides from about 5 ppm to 10,000 ppm, in one embodiment from about 100 to 3000 ppm, of fluoride ions in the total composition.

The compositions of the present invention may include a stannous ion source. The stannous ions may be provided from stannous fluoride and/or other stannous salts. Stannous fluoride has been found to help in the reduction of gingivitis, plaque, sensitivity, and in improved breath benefits. The stannous ions provided in an oral composition will provide efficacy to a subject using the composition. Although efficacy could include benefits other than the reduction in gingivitis, efficacy is defined as a noticeable amount of reduction in in situ plaque metabolism. Formulations providing such efficacy typically include stannous levels provided by stannous fluoride and/or other stannous salts ranging from about 3,000 ppm to about 15,000 ppm stannous ions in the total composition. Below about 3,000 ppm stannous the efficacy of the stannous is not sufficient. The stannous ion is present in an amount of from about 4,000 ppm to about 12,000 ppm, in one embodiment from about 5,000 ppm to about 10,000 ppm. Other stannous salts include organic stannous carboxylates, such as stannous acetate, stannous gluconate, stannous oxalate, stannous malonate, stannous citrate, stannous ethylene glycoxide, stannous formate, stannous sulfate, stannous lactate, stannous tartrate, and the like. Other stannous ion sources include, stannous halides such as stannous chlorides, stannous bromide, stannous iodide and stannous chloride dihydride. In one embodiment the stannous ion source is stannous fluoride in another embodiment, stannous chloride dihydrate. The combined stannous salts may be present in an amount of from about 0.01% to about 11%, by weight of the compositions. The stannous salts may typically be present in an amount of from about 0.1% to about 7%, in one embodiment from about 1% to about 5%, and in yet another embodiment from about 1.5% to about 3%, by weight of the composition.

Anti-microbial agents can also be present in the denture care composition of the present invention. Such agents may include, but are not limited to: 5-chloro-2-(2,4-dichlorophenoxy)-phenol, commonly referred to as Triclosan, and described in *The Merck Index*, 11th ed. (1989), pp. 1529 (entry no. 9573) in U.S. Pat. No. 3,506,720, and in European Patent Application No. 0,251,591 of Beecham Group, PLC,; 8-hydroxyquinoline and its salts; copper II compounds, including, but not limited to, copper(II) chloride, copper(II) sulfate, copper(II) acetate, copper(II) fluoride and copper(II) hydroxide; phthalic acid and its salts including, but not limited to those disclosed in U.S. Pat. No. 4,994,262, preferably magnesium monopotassium phthalate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; iodine; sulfonamides; bisbiguanides; phenolics; delmopinol, octapinol, and other piperidino derivatives; nicin preparations; zinc/stannous ion agents; nystatin; grapefruit extracts; apple extracts; thyme oil; thymol; antibiotics such as augmentin, amoxicillin, tetracycline, doxycycline, minocycline, metronidazole, neomycin, kanamycin, and clindamycin; analogs and salts of the above; essential oils including thymol, geraniol, carvacrol, citral, hinokitiol, eucalyptol, catechol (particularly 4-allyl catechol) and mixtures thereof; methyl salicylate; hydrogen peroxide; metal salts of chlorite; and mixtures of all of the above.

The compositions of the present invention may include an anti-plaque agent such as stannous salts, copper salts, strontium salts, magnesium salts or a dimethicone copolyol. The dimethicone copolyol is selected from C12 to C20 alkyl dimethicone copolyols and mixtures thereof. In one embodiment the dimethicone copolyol is cetyl dimethicone copolyol marketed under the Trade Name Abil EM90. The dimethicone copolyol is generally present in a level of from about 0.001% to about 25%, in one embodiment from about 0.01% to about 5% and in another embodiment from about 0.1% to about 1.5% by weight of the composition.

Anti-inflammatory agents can also be present in the compositions of the present invention. Such agents may include, but are not limited to, non-steroidal anti-inflammatory agents oxicams, salicylates, propoionic acids, acetic acids and fenamates. Such NSAIDs include but are not limited to Ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone, phenylbutazone and acetaminophen. Use of NSAIDs such as Ketorolac are claimed in U.S. Pat. No. 5,626,838, issued May 6, 1997. Disclosed therein are methods of preventing and, or treating primary and reoccurring squamous cell carcinoma of the oral cavity or oropharynx by topical administration to the oral cavity or oropharynx of an effective amount of an NSAID. Suitable steroidal anti-inflammatory agents include corticosteroids, such as fluccinolone, and hydrocortisone.

Nutrients may improve the condition of the oral cavity and can be included in the compositions of the present invention. Nutrients include minerals, vitamins, oral nutritional supplements, enteral nutritional supplements, and mixtures thereof. Useful minerals include calcium, phosphorus, zinc, manganese, potassium and mixtures thereof. Vitamins can be included with minerals or used independently. Suitable vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Oral nutritional supplements include amino acids, lipotropics, fish oil, and mixtures thereof. Amino acids include, but are not limited to L-Tryptophan, L-Lysine, Methionine, Threonine, Levocarnitine or L- carnitine and mixtures thereof. Lipotropics include, but are not limited to, choline, inositol, betaine, linoleic acid, linolenic acid, and mixtures thereof. Fish oil contains large amounts of Omega-3 (N-3) polyunsaturated fatty acids, eicosapentaenoic acid and docosahexaenoic acid. Enteral nutritional supplements include, but are not limited to, protein products, glucose polymers, corn oil, safflower oil, medium chain triglycerides. Minerals, vitamins, oral nutritional supplements and enteral nutritional supplements are described in more detail in *Drug Facts and Comparisons* (loose leaf drug information service), Wolters Kluer Company, St. Louis, Mo., © 1997, pps. 3–17 and 54–57.

A whitening agent may be included in the present invention. The actives suitable for whitening are selected from the group consisting of peroxides, metal chlorites, perborates, percarbonates, peroxyacids, persulfates such as oxones, and combinations thereof. Suitable peroxide compounds include hydrogen peroxide, urea peroxide, calcium peroxide, carbamide peroxide, and mixtures thereof. In one embodiment the peroxide compound is carbamide peroxide. Suitable metal chlorites include calcium chlorite, barium chlorite, magnesium chlorite, lithium chlorite, sodium chlorite, and potassium chlorite. Additional whitening actives may be hypochlorite and chlorine dioxide. In one embodiment the chlorite is sodium chlorite. In another embodiment the percarbonate is sodium percarbonate. This level is generally used in compositions of the present invention at levels from about 0.01% to about,40%, in one embodiment from about 0.1% to about 20%, in another embodiment from about 0.5% to about 10%, and in yet another embodiment from about 4% to about 7% of the composition.

Antioxidants are generally recognized as useful in denture care compositions. Antioxidants are disclosed in texts such as Cadenas and Packer, *The Handbook of Antioxidants,* © 1996 *by Marcel Dekker, Inc.* Antioxidants that may be included in the present invention include, but are not limited to Vitamin E, ascorbic acid, Uric acid, carotenoids, Vitamin A, flavonoids and polyphenols, herbal antioxidants, melatonin, aminoindoles, lipoic acids and mixtures thereof.

Antiviral actives useful in the present invention include any known actives that are routinely used to treat viral infections. Such antiviral actives include, but are not limited to: phosphonoformic acid; cyosine derivatives; purine analoglogues, such as adenosine, guanosine and inosine analogues; pyrimidine bases, such as citidine and thymidine; amantadines; rimantadine HCl; ribavirin; zanamivir; oseltamivir phosphate; trifluridine; heterocyclic dyes; acyclovir; famciclovir; valacyclovir, cidofovir; ganciclovir; levimisole; idoxuridine; lipophilic β-ketones; and thiosemicarbazones. These antiviral actives are described in *Drug Facts and Comparisons* (loose-leaf drug information service), Wolters Kluwer Company, St. Louis, Mo., ©2001, pp. 1400–1423 (b), and in *Kirk-Othmer, Encyclopedia of Chemical Technology*, Fourth Edition, Volume 3, Wiley-Interscience Publishers (1992), pp. 576–607, both incorporated herein by reference in their entirety. Specific examples include antiviral actives disclosed in U.S. Pat. No. 5,747,070, to Majeti, incorporated herein by reference in its entirety. Said patent discloses the use of stannous salts to control viruses. Stannous salts are described in more detail above. While stannous fluoride may be used as an antiviral agent, it is typically used only in combination with another stannous halide or one or more stannous carboxylates or another therapeutic agent.

Anti-fungal agents can also be included in the denture care compositions of the present invention. Anti-fungals are agents that destroy or inhibit the growth of fungi. Antifungal agents useful in the present invention are those drugs for systemic mycoses or drugs for mucocutaneuos infections. Suitable antifungals include but are not limited to nystatin; miconazole; econazole nitrate; clotrimazole; and flucytosine. In one embodiment the antifungal agent is nystatin.

Anti-pain or desensitizing agents can also be present in the denture compositions of the present invention. Analgesics are agents that relieve pain by acting centrally to elevate pain threshold without disturbing consciousness or altering other sensory modalities. Such agents may include, but are not limited to, strontium chloride, potassium nitrate, sodium nitrate, sodium fluoride, acetanilide, phenacetin, acertophan, thiorphan, spiradoline, aspirin, codeine, thebaine, levorphenol, hydromorphone, oxymorphone, phenazocine, fentanyl, buprenorphine, butaphanol, nalbuphine, pentazocine, natural herbs such as gall nut, Asarum, Cubebin, Galanga, scutellaria, Liangmianzhen, Baizhi, etc. Anesthetic agents, or topical analgesics, such as acetaminophen, sodium salicylate, trolamine salicylate, lidocaine and benzocaine may also be present. These analgesic actives are described in detail in *Kirk-Othmer, Encyclopedia of Chemical Technology*, Fourth Edition, Volume 2, Wiley-Interscience Publishers (1992), pp. 729–737, incorporated herein by reference in its entirety.

Histamine-2 (H-2 or H2) receptor antagonist compounds (H-2 antagonists) may be used in the compositions of the present invention. As used herein, selective H-2 antagonists are compounds that block H-2 receptors, but do not have meaningful activity in blocking histamine-1 (H-1 or H1) receptors. Selective H-2 antagonists stimulate the contraction of smooth muscle from various organs, such as the gut and bronchi; this effect can be suppressed by low concentrations of mepyramine - a typical antihistaminic drug. The H-2 antagonists useful in the present invention are those that blockade the receptors involved in mepyramine-insensitive, non-H-1 (H-2), histamine responses and do not blockade the receptors involved in mepyramine-sensitive histamine responses. Selective H-2 antagonists include compounds meeting the above criteria which are disclosed in U.S. Pat. Nos. 5,294,433 and 5,364,616 both to Singer, et al., and assigned to The Procter & Gamble Company, wherein the selective H-2 antagonist is selected from the group consisting of cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY-25368 (SKF-94482), BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, and HB-408. Related suitable H-2 antagonists include burimamide and metiamide.

The denture compositions of the present invention may also include one or more components that provide fragrance, and/or sensate benefit (warming or cooling agents). Suitable components include menthol, menthyl lactate, wintergreen oil, peppermint oil, spearmint oil, leaf alcohol, camphor, clove bud oil, eucalyptus oil, anethole, methyl salicylate, eucalyptol, cassia, 1-8 menthyl acetate, eugenol, oxanone, alpha-irisone, propenyl guaethol, cinnamon, thymol, linalool, benzaldehyde, cinnamaldehyde glycerol acetal known as CGA, and mixtures thereof, as well as coolants. The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23, "and mixtures thereof. Additional preferred coolants are selected from the group consisting of menthol, 3-1-menthoxypropane-1,2-diol known as TK-10, manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al. WS-3 and other agents are described in U.S. Pat. No. 4,136,163, Watson, et al. The disclosures of both are herein incorporated by reference.

Pigments may be added to the compositions herein to more precisely indicate the locations at which the composition has actually been in contact. Additionally, these substances may be suitable for modifying the color of the denture to satisfy the consumer. These substances comprise particles that when applied on the tooth surface modify that surface in terms of absorption and, or reflection of light. Such particles provide an appearance benefit when a film containing such particles is applied over the surfaces of the denture. Pigments, dyes, colorants and lakes may also be added to modify the appearance of the compositions herein to render the product more acceptable to the consumer. Appropriate pigment levels are selected for the particular impact that is desirable to the consumer. For example, for dentures that are particularly dark or stained one would typically use pigments in sufficient amounts to lighten the teeth. On the other hand, where individual teeth or spots on the teeth are lighter than other teeth, pigments to darken the denture may be useful. The levels of pigments and colorants may be in the range of about 0.001% to about 20%, in one embodiment from about 0.01% to about 15%, and in another embodiment from about 0.1 % to about 10% by total weight of the composition.

Pigments and colorants include inorganic white pigments, inorganic colored pigments, pearling agents, filler powders and the like; see Japanese Published Patent Application Kokai No. 9 [1997]-100215, published Apr. 15, 1997, incorporated herein by reference. Specific examples are selected from the group consisting of talc, mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. In one embodiment the pigments and colorants are those selected from the group consisting of titianium dioxide, bismuth oxychloride, zinc oxide, Opatint D&C Red 27, CI 16185:1 Acid 27 Lake E123, CI14720:1 Carmosoisine Aluminum Lake E122, Red 7 Lake, or Red 30 Lake, and mixtures thereof.

The present invention may further comprise a viscosity modifier that inhibits settling and separation of components or controls settling in a manner that facilitates re-dispersion and may control flow properties. A viscosity modifier is particularly useful to keep denture care actives that are in particulate form suspended within the polybutene components of the present invention. Suitable viscosity modifiers herein include mineral oil, organo modified clays, petrolatum, silicas, and mixtures thereof. In one embodiment the viscosity modifier is silica. Where incorporated, the viscosity modifier is present in the polybutene component of the present invention at a level of from about 0.001% to about 75%, in one embodiment from about 0.01% to about 50%, and in another embodiment from about 0.1% to about 25% of the composition.

The denture composition may optionally further comprise one or more flavorants. These flavoring agents can be chosen from synthetic flavoring liquid and/or oils derived from plants leaves, flowers, fruits and so forth, and combinations thereof. Representative flavoring liquids include: vanillin, sage, marjoram, parsley oil, spearmint oil, cinnamon oil, oil of wintergreen (methylsalicylate), peppermint oils clove oil, bay oil, anise oil, and eucalyptus oil. Also useful are artificial, natural or synthetic fruit flavors such as citrus oil including lemon, orange, banana, grape, lime, apricot and grapefruit and fruit essences including apple, strawberry, cherry, orange, pineapple and so forth; bean and nut derived flavors such as coffee, cocoa, cola, peanut, almond and so forth. Additionally, flavor adsorbed onto a hydrophilic matrix may be included, e.g. "spray-dried" flavors. Furthermore, encapsulated flavors may be included. The amount of flavorant employed is normally a matter of preference subject to such factors as flavor type and strength of flavor desired. Flavorants may be present in amounts up to about 4%, in one embodiment about 0.05% to about 3.0%, in another embodiment about 0.8% to about 2.5%, by weight of the total composition.

The denture composition may optionally further comprise one or more sweeteners. Suitable sweeteners include natural and artificial, water soluble, water insoluble and intense sweeteners. The sweetening agent may comprise dextrose, sucrose, maltose, dextrin, dried invert sugar, mannose, xylose, ribose, glucose, fructose, levulose, galactose, corn syrup, high fructose corn syrup, corn syrup solids, partially hydrolyzed starch, aspartame, saccharin, sugar alcohols such as sorbitol, mannitol, xylitol, maltitol, isomalt, and hydrogenated starch hydrolysate or combinations thereof. Natural artificial intense sweeteners such as dipeptide based intense sweeteners, monellin, thaumaoccous danielli, and L-aspartyl L-phenylalanine methyl ester and soluble saccharin salts may be incorporated as sweeteners. The amount of the sweetener will vary with the type of sweetener selected and the desired level of sweetness. Sweetening agents and flavoring agents are typically used in denture care compositions at levels of from about 0.005% to about 5%, by weight of the total composition.

Additional actives suitable for use in the present invention may include, but are not limited to, insulin, steroids, herbal and other plant derived remedies, and anti-neoplastics. Additionally, anti-gingivitis or gum care agents known in the art may also be included. Components, other than polybutene, which impart a clean feel to the teeth may optionally be included. These components may include, for example, baking soda or Glass-H. Also, it is recognized that in certain forms of therapy, combinations of these above-named agents may be useful in order to obtain an optimal effect. Thus, for example, an anti-microbial and an anti-inflammatory agent may be combined in a single chewing gum or confection piece to provide combined effectiveness.

Denture Care Carriers

In preparing the present composition, one or more non-aqueous denture care carriers may be optionally added. Such materials are well known in the art and are readily chosen by one skilled in the art based on the physical and aesthetic properties desired for the composition being prepared. These carriers may be included at levels that do not interfere or prohibit the surface conditioning. Typically the level of non-aqueous denture care carrier is about 0.001% to about 90%, in one another embodiment from about 0.01% to about 75% and in yet another embodiment from about 0.1% to about 50%, by total weight of the composition.

The non-aqueous denture care carrier is generally any chemical in any physical form that does not contain water. The non-aqueous vehicle is selected from the group consisting of liquid petrolatum, petrolatum, mineral oil, glycerin, natural and synthetic oils, fats, silicone and silicone derivatives, natural and synthetic waxes such as animal waxes like beeswax, lanolin and shellac, hydrocarbons, hydrocarbon derivatives, vegetable oil waxes such as camauba, candelilla and bayberry wax, vegetable oils such as caprylic/capric triglycerides; in another embodiment is selected from the group consisting of liquid petrolatum, petrolatum, mineral oil, vegetable oils such as corn, soy bean, cottonseed, castor, palm and coconut oils and animal oil such as fish oil and oleic acid, and mixtures thereof; in yet another embodiment is mineral oil.

Caprylic/capric triglycerides are triglycerides of medium chain fatty acids where the —C=O—R group is 8–10 carbons and is obtained by the addition of glycerol to a mixture of capric and caprylic acids:

Capric Acid: $CH_3(CH_2)_8CO_2H$ 

Caprylic Acid: $CH_3(CH_2)_6CO_2H$ 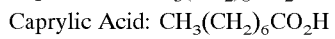

Therefore, vegetable oils comprised of saturated medium chain fatty acids such as caprylic acid, capric acid and mixtures thereof, can be used in the present invention. These vegetable oils and other non-aqueous carriers for denture care compositions are further described in U.S. Pat. No. 5,561,177 to Khaledi, at el., which is incorporated herein by reference in its entirety.

Other suitable denture care carriers include preservatives such as methyl and propyl parabens, thickeners such as silicon dioxide, and polyethylene glycol.

Method of Preparation

The denture composition is suitably made as follows: Combine the polybutene and any denture care active ingredients into a mixing vessel and mix well with any means known within the art, for example, with spatula or mixer. Heat the composition, if desired, to facilitate mixing. Continue mixing the composition until homogenous. Where a denture care active is included in solid particulate form, the addition of a viscosity modifier, such as silica, may be appropriate to keep the particulate dispersed and suspended within the composition. Flavorants or sweeteners may also be added as desired.

Where a denture care carrier is desired within the composition of the present invention, the denture care carrier component and the polybutene containing component are prepared separately and then emulsified to form a single phase composition. Where a dual or multi phase composition is desired, the components are, typically, physically separated until the time of administration to the denture. The denture care carrier component is prepared using conventional methods. Generally, blending of the desired ingredients until homogenous is sufficient. A denture care active may also be incorporated within the denture care carrier component of the present invention.

The polybutene component of the denture care kits is prepared in the same manner as the denture compositions above, with the addition of the denture care active being optional. In one embodiment, a container such as a jar, cup, can, tube, aerosol can, tub, pump, bottle or any other liquid holding or dispensing means, is filled with the polybutene component. Sample accompanying instructions for the use of the kit would read: "Apply the denture care composition directly to the denture or dental plate when removed from the oral cavity. Apply a sufficient amount of the composition to coat the denture, directly to the denture surface by finger, brush, dental stick, or cotton swab. It is not necessary to excessively clean, by brushing, or dry the denture or dental plate either before or after application." In another denture care kit, the polybutene component is placed within any suitable applicator, such as a tube or pen applicator, for direct application to the artificial teeth. Where an applicator is included with the denture care kit of the present invention, sample instructions would read: "Apply the denture care composition directly to the denture or dental plate. Apply a sufficient amount to sufficiently coat the artificial teeth by use of the enclosed applicator. It is not necessary to excessively clean, by brushing, or dry the denture or dental plate either before or after application."

Method of Use

In practicing the denture care kits and composition of the present invention, the user removes the denture from the oral cavity and applies the denture care composition disclosed herein directly to the surface of the denture. Where an applicator is included in the denture care kit, the polybutene composition can be applied using the brush, pen applicator, dropper, doe's foot applicator or other supplied application device. Where an applicator is not provided with the denture care kit or composition of the present invention, the polybutene component may also be applied by finger, cotton swab, or dental stick or the like or by dipping the denture into the polybutene composition.

It is not necessary to prepare the denture before applying the composition of the present invention. For example, the user may or may not choose to brush or cleanse the denture before applying the composition. The surfaces of the denture are neither required to be dried nor to be excessively wet with saliva or water prior to application. However, it is believed that adhesion to the denture surfaces will be improved if the surfaces are drier when the composition is applied.

EXAMPLES

The following non-limiting examples further illustrate and describe the embodiments of the subject invention wherein both essential and optional ingredients are combined. It is to be understood that the examples are given solely for the purpose of illustration and are not to be construed as limiting the scope of the present invention, as many variations thereof are possible without departing from the spirit and scope of the invention.

The polybutene is combined with the denture care active (if included), upon weighing, into a mixing vessel and mixed well with a mechanical mixer. The composition is mixed until homogenous. Where the denture care active is in solid particulate form, a viscosity modifier, such as silica, may be added to the mixture in the same manner and mixing continues until homogenous. Values given below are in weight percent of the polybutene component of the denture care kits and composition of the present invention.

Examples 1–6

| Ingredients | Ex. 1 | Ex. 2 | Ex. 3 | Ex. 4 | Ex. 5 | Ex. 6 |
|---|---|---|---|---|---|---|
| Polybutene[1] | 87% | 99.7% | 99.742% | 99.56% | 99.84% | 75.00% |
| Glass-H | | 13% | | | | 25.00% |
| Triclosan | | 0.3% | | | | |
| Thymol | | | | 0.064% | | |
| Eucalyptol | | | | 0.092% | | |
| Menthol | | | | 0.060% | 0.12% | |
| Methyl Salicylate | | | | 0.042% | | |
| Menthyl Lactate | | | | | 0.17% | |
| Peppermint | | | | | 0.15% | |
| 8-hydroxy-quinoline salts | | | | | | 0.10% |
| $CuCl_2.2H_2O$ | | | | | | 0.06% |

[1]Indopol H-300, MW = 1330, trade name of BP Amoco Chemicals (Chicago, IL).

Examples 7–12

| Ingredients | Ex. 7 | Ex. 8 | Ex. 9 | Ex. 10 | Ex. 11 | Ex. 12 |
|---|---|---|---|---|---|---|
| Polybutene[2] | 90% | 80% | 99.955% | 99.757% | 99.97% | 99.1% |
| CPC | | | 0.045% | | | 0.09% |
| Apple Extract | 10% | | | | | |
| Baking Soda | | 20% | | | | |
| Sodium Fluoride | | | | 0.243% | | |
| Nystatin | | | | | 0.03% | |

[2]Indopol H-40, MW = 750, trade name of BP Amoco Chemicals (Chicago, IL).

Examples 13–19

| Ingredients | Ex. 13 | Ex. 14 | Ex. 15 | Ex. 16 | Ex. 17 | Ex. 18 | Ex. 19 |
|---|---|---|---|---|---|---|---|
| Polybutene[3] | 90% | 90% | 90% | 99.76% | 99.76% | 99.76% | 99.066% |
| Carvacrol | 10% | | | | | | |
| Grape Seed Extract | | 10% | | | | | |
| Opatint D&C Red 27 | | | | 0.24% | | | |
| Red 7 | | | | | 0.24% | | |
| Red 30 | | | | | | 0.24% | |
| Grapefruit Seed Extract | | | 10% | | | | |
| Calcium Peroxide | | | | | | | 0.934% |

[3]Indopol H-100, MW = 940, trade name of BP Amoco Chemicals (Chicago, IL).

Examples 20–25

| Ingredients | Ex. 20 | Ex. 21 | Ex. 22 | Ex. 23 | Ex. 24 | Ex. 25 |
|---|---|---|---|---|---|---|
| Polybutene[4] | 90% | 99% | 99.47% | 97.95% | 99.24% | 92.5% |
| Xylitol | 10% | | | | | |
| Chlorexidine | | 1% | | | | |
| Stannous Fluoride | | | 0.53% | | | |
| Tetra Sodium Pyrophosphate | | | | 2.05% | | |
| Eugenol | | | | | 7.5% | |
| Mono Fluoro Phosphate | | | | | | 0.76% |

[4]Indopol H-1900, MW = 2270, trade name of BP Amoco Chemicals (Chicago, IL).

Examples 26–33

| Ingredients | Ex. 26 | Ex. 27 | Ex. 28 | Ex. 29 | Ex. 30 | Ex. 31 | Ex. 32 | Ex. 33 |
|---|---|---|---|---|---|---|---|---|
| Polybutene[5] | 81% | 81% | 81% | 80% | 56% | 80% | 81% | 100% |
| Sodium Percarbonate | 19% | | | | 19% | | | |
| Urea Peroxide | | 19% | | | | | | |
| Calcium Peroxide | | | 19% | | | | | |
| Silica | | | | 1% | | | | |
| Petrolatum | | | | | 25% | | | |
| Benzocaine | | | | | | 20% | | |
| (Polyvinvl-Pyrrolidone) Peroxide Complex | | | | | | | 19% | |

[5]Indopol H-300, MW = 1330, trade name of BP Amoco Chemicals (Chicago, IL).

Examples 34–37

| Ingredients | Ex. 34 | Ex. 35 | Ex. 36 | Ex. 37 |
|---|---|---|---|---|
| Polybutene[6] | 63.76% | 54.5% | 60.5% | 61.5% |
| Petrolatum | 10.00% | 12.5% | 12.5% | 12.5% |
| Silica | 1.00% | 1.0% | 1.0% | 1.0% |
| Glass-H | 25.00% | 25.0% | 25.0% | 25.0% |
| Peppermint Oil | | 6.0% | | |
| Asparatame | | 1.0% | 1.0% | |
| Opatint 27 | 0.24% | | | |

[6]Indopol H-300, MW = 1330, trade name of BP Amoco Chemicals (Chicago, IL).

It should be understood that the above-described polybutene-containing compositions may be combined in any ratio and used in the compositions and kits herein. It should also be understood that these examples are non-limiting. The level of polybutene and denture care actives exemplified herein may vary by as much as 80% and still be suitable for use in the compositions and kits disclosed herein.

Where a denture care carrier is incorporated in the compositions of the present invention, the composition is, likewise, made by blending the desired ingredients until the mixture is homogenous. In the following examples, values given are in total weight percent of the denture care composition of the present invention.

| Ingredient | Ex. A | Ex. B | Ex. C | Ex. D | Ex. E | Ex. F | Ex. G | Ex. H |
|---|---|---|---|---|---|---|---|---|
| Polybutene[7] | 99% | 90% | 75% | 89% | 99% | 90% | 75% | 89% |
| Petrolatum | 1% | 10% | | 10% | | | | |
| Silica | | | 1% | | | | | 1% |
| Silicone Oil | | | 25% | | | 10% | | |
| Mineral Oil | | | | 1% | | 25% | 10% |

[7]Indopol H-300, MW = 1330, trade name of BP Amoco Chemicals (Chicago, IL).

The dentures or artificial teeth that are treated with the denture care kits and compositions described above should be exposed to the polybutene containing solution for a period of about 10 seconds to several hours, as in overnight treatment.

It is understood that the examples and embodiments described herein are for illustrative purposes only and that various modifications or changes in light thereof will be suggested to one of skill in the art without departing from the scope of the present invention.

What is claimed is:

1. A denture care composition comprising.
   (a) polybutene with a molecular weight of about 300 to about 3000;
   (b) one or more denture care actives; and
   (c) a non-aqueous, oily denture care carrier;
   wherein the composition is not self-supporting, is not a denture adhesive, chewing gum or on a flexible strip and wherein the composition is essentially free of a mucoadhesive, wherein said polybutene is a flowable liquid, which is non-mucoadhesive, non-bioadhesive, and which is not elastic, elastomeric, rubbery, or crosslinked, and which adheres to the hard surfaces of the denture.

2. The denture care composition according to claim 1 wherein the denture care carrier is selected from the group consisting of liquid petrolatum, petrolatum, mineral oil, vegetable oils such as corn, soy bean, cottonseed, castor, palm and coconut oils and animal oil such as fish oil and oleic acid, and mixtures thereof.

3. The denture care composition according to claim 1 wherein the denture care active ingredient is selected from the group consisting of anti-calculus agents; fluoride ion sources; stannous ion sources; whitening agents; anti-microbial, anti-plaque agents; anti-inflammatory agents; nutrients; antioxidants; anti-viral agents; anti-fungal agents; analgesic and anesthetic agents; H-2 antagonists; and mixtures thereof.

4. The denture care composition according to claim 3 wherein the denture care active ingredient is selected from the group consisting of triclosan, baking soda, sodium fluoride, potassium nitrate, sodium nitrate, nystatin, grapefruit seed extract, stannous fluoride, tetra sodium pyrophosphate, mono fluoro phosphate, polyphosphates, and celylpyridiwn chloride.

5. The denture care composition according to claim 4 wherein the polyphosphate is sodium hexametaphosphate.

6. The denture care composition according to claim 3 wherein the denture care composition further comprises a viscosity modifier.

7. The denture care composition according to claim 1 wherein the polybutene has a molecular weight of about 500 to about 2200.

8. The denture care composition according to claim 7 wherein the polybutene has a molecular weight of about 750 to about 1500.

9. A method of coating the dentures by applying to the denture the denture care composition of claim 1.

10. A method of providing sustained release of therapeutic and cosmetic actives to oral cavity by applying to the dentures the denture care composition of claim 1.

11. A method of inhibiting and preventing gingivitis, caries, staining, fungi, bacteria and plaque build up in the oral cavity by applying to the dentures the denture care composition of claim 1.

12. A method of imparting a clean feel to the dentures by applying to the dentures the denture care composition of claim 1.

13. A method of imparting a clean feel to the dentures by applying to the dentures a denture care composition comprising polybutene and a denture care active, wherein the polybutene has a molecular weight of about 300 to about 3000.

14. The composition of claim 1 further comprising optional components selected from the group consisting of components other than polybutene which impart a clean feel to the teeth; fragrances and sensates; pigments, dyes, lakes and colorants; flavorants; sweeteners; and mixtures thereof.

15. The composition of claim 14 wherein the optional component is Opatint D&C Red 27.

* * * * *